United States Patent
Tran et al.

(10) Patent No.: US 12,144,489 B2
(45) Date of Patent: Nov. 19, 2024

(54) LIQUID LENS AUTO FOCUS FOR ENDOSCOPIC SURGERY VISUALIZATION

(71) Applicant: Stryker Corporation, Kalamazoo, MI (US)

(72) Inventors: Levey Trac Tran, Denver, CO (US); Chien Mien Pang, San Jose, CA (US); Ajay Ramesh, Pleasanton, CA (US); Rohit Subramanian, San Jose, CA (US); Pankaj Sharma, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 480 days.

(21) Appl. No.: 17/052,157

(22) PCT Filed: May 2, 2019

(86) PCT No.: PCT/US2019/030339
§ 371 (c)(1),
(2) Date: Oct. 30, 2020

(87) PCT Pub. No.: WO2019/213360
PCT Pub. Date: Nov. 7, 2019

(65) Prior Publication Data
US 2021/0058559 A1      Feb. 25, 2021

Related U.S. Application Data

(60) Provisional application No. 62/665,716, filed on May 2, 2018.

(51) Int. Cl.
*A61B 1/00* (2006.01)
*A61B 1/04* (2006.01)
(Continued)

(52) U.S. Cl.
CPC ........ *A61B 1/0019* (2013.01); *A61B 1/00009* (2013.01); *A61B 1/042* (2013.01);
(Continued)

(58) Field of Classification Search
CPC ... A61B 1/0019; A61B 1/00009; A61B 1/042; A61B 1/00188; A61B 1/00096;
(Continued)

(56) References Cited

U.S. PATENT DOCUMENTS

| 4,802,746 A | 2/1989 | Baba |
| 6,533,721 B1 | 3/2003 | Beutter |

(Continued)

FOREIGN PATENT DOCUMENTS

| FR | 2876267 A1 | 4/2006 |
| WO | 2007/033326 A2 | 3/2007 |

OTHER PUBLICATIONS

Carestream Dental. (2023) "Intraoral Cameras," located at https://www.carestreamdental.com/en-us/category/intraoral/intraoral-cameras/; 2 pages.

(Continued)

*Primary Examiner* — Timothy J Neal
*Assistant Examiner* — James Edward Boice
(74) *Attorney, Agent, or Firm* — Morrison & Foerster LLP

(57) ABSTRACT

A surgical camera system comprising: a camera head including a housing; an image sensor within the housing; and the housing including a liquid lens therein for focusing an image received in the housing prior to transmission of the image to the image sensor, and a fixed solid lens adjacent the liquid lens.

13 Claims, 10 Drawing Sheets

(51) Int. Cl.
*G02B 23/24* (2006.01)
*H04N 23/55* (2023.01)
*H04N 23/67* (2023.01)

(52) U.S. Cl.
CPC ......... *G02B 23/2484* (2013.01); *H04N 23/55* (2023.01); *H04N 23/673* (2023.01)

(58) Field of Classification Search
CPC .. H04N 23/673; H04N 23/55; G02B 23/2484; G02B 26/005; G02B 2/0006; B02B 3/0081
USPC .......................................................... 600/109
See application file for complete search history.

(56) References Cited

U.S. PATENT DOCUMENTS

| | | | |
|---|---|---|---|
| 7,553,020 B2 | 6/2009 | Goldfain et al. | |
| 7,734,160 B2 | 6/2010 | Sudo et al. | |
| 7,852,371 B2 | 12/2010 | Konstorum et al. | |
| 8,571,397 B2 | 10/2013 | Liu et al. | |
| 2008/0208003 A1* | 8/2008 | Miyagi | A61B 1/0052 600/146 |
| 2009/0072037 A1 | 3/2009 | Good et al. | |
| 2011/0013297 A1* | 1/2011 | Barnes | G03B 3/00 359/823 |
| 2011/0118610 A1* | 5/2011 | Kuiper | A61B 1/0019 600/476 |
| 2014/0002626 A1 | 1/2014 | Yu et al. | |
| 2014/0017625 A1* | 1/2014 | Liu | A61B 1/042 433/29 |
| 2014/0111628 A1 | 4/2014 | Yoshino et al. | |
| 2014/0364790 A1* | 12/2014 | Matsumoto | A61F 9/00772 604/8 |
| 2015/0057952 A1* | 2/2015 | Coombs | G01N 29/04 702/38 |
| 2016/0227994 A1 | 8/2016 | Gotsch et al. | |
| 2017/0119238 A1* | 5/2017 | Gao | G02B 23/243 |
| 2017/0230556 A1* | 8/2017 | Bormet | G06T 7/35 |
| 2017/0239012 A1 | 8/2017 | Wood et al. | |
| 2017/0351103 A1 | 12/2017 | Duckett | |
| 2019/0000308 A1* | 1/2019 | Duckett, III | A61B 1/00105 |
| 2019/0310490 A1* | 10/2019 | Park | G03B 13/32 |
| 2021/0014428 A1* | 1/2021 | Hyun | G02F 1/29 |
| 2021/0041604 A1* | 2/2021 | Choi | H04N 23/54 |
| 2021/0263259 A1* | 8/2021 | Seo | H04N 23/951 |

OTHER PUBLICATIONS

Cognex. (2023) "Liquid Lens Technology—Dynamic autofocusing system," located at https://www.cognex.com/products/leading-technology/liquid-lens-technology?rdr=lgcy; 6 pages.

Corning. (2023) "Corning® Varioptic® Lenses (Variable and AutofocusLenses) | Liquid Lens Technology" located at https://www.coming.com/worldwide/en/products/advanced-optics/product-materials/corning-varioptic-lenses.html; 17 pages.

International Preliminary Report on Patentability dated Nov. 3, 2020, directed to International Application No. PCT/US2019/030339; 8 pages.

International Search Report and Written Opinion mailed Aug. 28, 2019, directed to International Application No. PCT/US2019/030339; 16 pages.

Invitation to Pay Additional Fees and, Where Applicable, Protest Fee mailed Jul. 2, 2019, directed to International Application No. PCT/US2019/030339; 10 pages.

Optilux. (2015) "Products," located at "https://web.archive.org/web/20150222074639/http://optilux.com/products/"; 2 pages.

PixelLink. (2015) "PixelLink—Industrial Cameras," located a https://web.archive.org/web/20151128020816/http://pixelink.com/; 2 pages.

Decision to Grant dated Jan. 5, 2024, directed to EP Application No. 19724020,3; 2 pages.

Intention to Grant dated Aug. 10, 2023, directed to EP Application No. 19 724 020.3; 8 pages.

European Search Report mailed Jul. 1, 2024, directed to EP Application No. 24153502.0; 8 pages.

* cited by examiner

LIQUID LENS AUTO FOCUS FOR ENDOSCOPIC SURGERY VISUALIZATION

CROSS-REFERENCE TO RELATED APPLICATIONS

This application is a national stage application under 35 USC 371 of International Application No. PCT/US2019/030339, filed May 2, 2019, which claims priority to U.S. Provisional Application No. 62/665,716, filed May 2, 2018, the contents of each of which are incorporated by reference herein in their entirety.

FIELD

The present disclosure generally relates to medical imaging, and more specifically to use of auto focus in endoscopic surgery visualization.

BACKGROUND

Medical instruments or tools are utilized during surgery for various purposes. Some of these surgical tools may be used in what are generally termed endoscopic procedures. Endoscopy in the medical field allows internal features of the body of a patient to be viewed without the use of traditional, fully invasive surgery. Endoscopic imaging systems incorporate endoscopes so as to enable a surgeon to view a surgical site, and endoscopic tools enable non-invasive surgery at the site. Such tools may be shaver-type devices which mechanically cut bone and hard tissue, or radio frequency (RF) probes which are used to remove tissue via ablation or to coagulate tissue to minimize bleeding at the surgical site, for example.

In endoscopic surgery, the endoscope is placed in the body at the location at which it is necessary to perform a surgical procedure. Other surgical instruments, such as the endoscopic tools mentioned above, are also placed in the body at the surgical site. A surgeon views the surgical site through the endoscope in order to manipulate the tools to perform the desired surgical procedure. Some endoscopes are usable along with a camera head for the purpose of processing the images received by the endoscope. The eye piece of such an endoscope is typically coupled to a camera head, which is connected to a camera control unit.

The development of endoscopes and their companion surgical tools has made it possible to perform minimally invasive surgery that eliminates the need to make a large incision in the patient to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

It is important that, during a surgical procedure, an endoscope can be focused so that a surgeon and staff can clearly see the surgical site. Current endoscopic camera systems require user input to perform mechanical actuation of a focus ring or lever to change the image focus. Such a focus ring or lever actuation causes a fixed focal length lens to axially translate, thus changing where the light transmitted from the endoscope focuses the image on the sensor. This requires the camera operator to spend additional time achieving a focused image due to the requirement of the steps of determining the correct direction to actuate the focus ring or lever, actuating the focus ring or lever in the correct direction until image focus is achieved, or if the focus ring or lever is actuated past the focus point then the focus ring or lever must be actuated in the reverse direction to reach the focus point. Such a procedure requires that the user change the position of his or her hand that is holding the camera to reach the focusing mechanism on the coupler, and typically bring in his or her second hand to the coupler in order to change the image focus. The procedure can result in loss of visualization of the surgical site momentarily due to camera head movement and delay in the surgical procedure.

Consumer grade cameras, such as DSLR cameras, sometimes include an auto focus system. There are two types of auto focus systems in DSLR consumer cameras. The first is an active auto focus which works by radiating light (usually a red beam) on the subject. The red light reflects back into the camera where it is captured by the main camera sensor and another sensor. Such cameras contain an algorithm to analyze the image data and uses triangulation to determine the distance between the camera and the subject. After the distance is calculated, the camera adjusts the focus lens to the focus position. An active auto focus can only be used with stationary, non-moving objects and requires an additional light source and an additional sensor which results in a significantly larger camera housing.

The second type of auto focus in consumer DSLR cameras is a passive auto focus. A passive auto focus works by either using phase detection using special sensors within the camera to detect contrast from the light that goes through the lens, or contrast detection which uses the main camera sensor to detect contrast from the light that goes through the lens. These cameras contain an algorithm to analyze the sharpness in a particular part of an image scene and adjust the lens focus until focus is achieved. As with active auto focus, the phase and/or contrast detection systems require an increased camera head housing size and the use of motors to drive the movement of the focusing lens. Having such a motor may also increase the probability of failure of the equipment and generates noise when it moves.

SUMMARY

Embodiments of the camera herein use a liquid-filled lens (hereinafter "liquid lens") to achieve variable focus automatically and nonmechanically. According to some embodiments, the liquid lens is housed inside the camera housing of the camera system and is comprised of two immiscible liquids, oil and water, trapped in a closed cell. Preferably, a solid lens assembly is placed directly after the liquid lens in the optical path.

According to some embodiments, in operation, the liquid lens receives a voltage signal via a cable to adjust focus. The signal can be based on an analysis of image signal data to determine the focus of the image. An algorithm can be used, which is preferably in a camera control unit, to determine the focus which may be through a continuous search mode or a trigger image focus mode.

According to some embodiments, liquid lenses use electrowetting which uses voltage to modify the surface tension of the conductive liquid (preferably water) on a solid surface. The radius of curvature of the liquid-liquid interface can be varied, thus changing the optical power of the lens. The liquid lens refracts the light transmitted from the endoscope and focuses the image on the sensor.

Described herein are variations of liquid lens auto focus systems and methods for use in endoscopic surgery visualization. Generally, in one variation a surgical camera system is provided which comprises a camera head including a housing, an image sensor within the housing, and the housing including a liquid lens therein for focusing an image received in the housing prior to transmission of the image to the image sensor, and a fixed solid lens adjacent the liquid lens.

Also provided is a surgical camera system, according to some embodiments, that includes a camera assembly including a housing having an outer wall defining a space in the housing, an image sensor disposed within the housing, an optical path within the housing capable of allowing an optical image to travel from a surgical site to the image sensor, and at least one lens assembly within the optical path. The lens assembly may include a liquid lens and at least one fixed solid lens adjacent the liquid lens.

A method of focusing a medical camera according to some embodiments is also provided. The method includes providing a camera head assembly including a housing, an image sensor in the housing, a lens assembly in the housing including a liquid lens, and a liquid lens driver capable of sending a voltage to the liquid lens; providing a camera control unit which includes an algorithm capable of calculating a desired voltage based on image signal data and transmitting a signal to the liquid lens driver; the image sensor obtaining an optical image; the image sensor converting the optical image to optical image data; the image sensor transmitting the optical image data to the camera control unit; the algorithm analyzing the optical image data and based on the analysis forwarding a signal to the liquid lens driver; and the liquid lens driver transmitting a voltage to the liquid lens based on the signal received from the camera control unit. The method of the algorithm can include determining if liquid lens hardware is present, and commanding an initial voltage for the liquid lens hardware if it is present; setting a high threshold focus metric; the camera capturing an image frame and converting the image frame to data; calculating a focus metric of the image frame data and comparing the image frame data focus metric to the high threshold focus metric; and if the image frame data focus metric is higher than the high threshold focus metric, commanding a change in voltage to be delivered to the liquid lens hardware.

DETAILED DESCRIPTION

Figure 1:
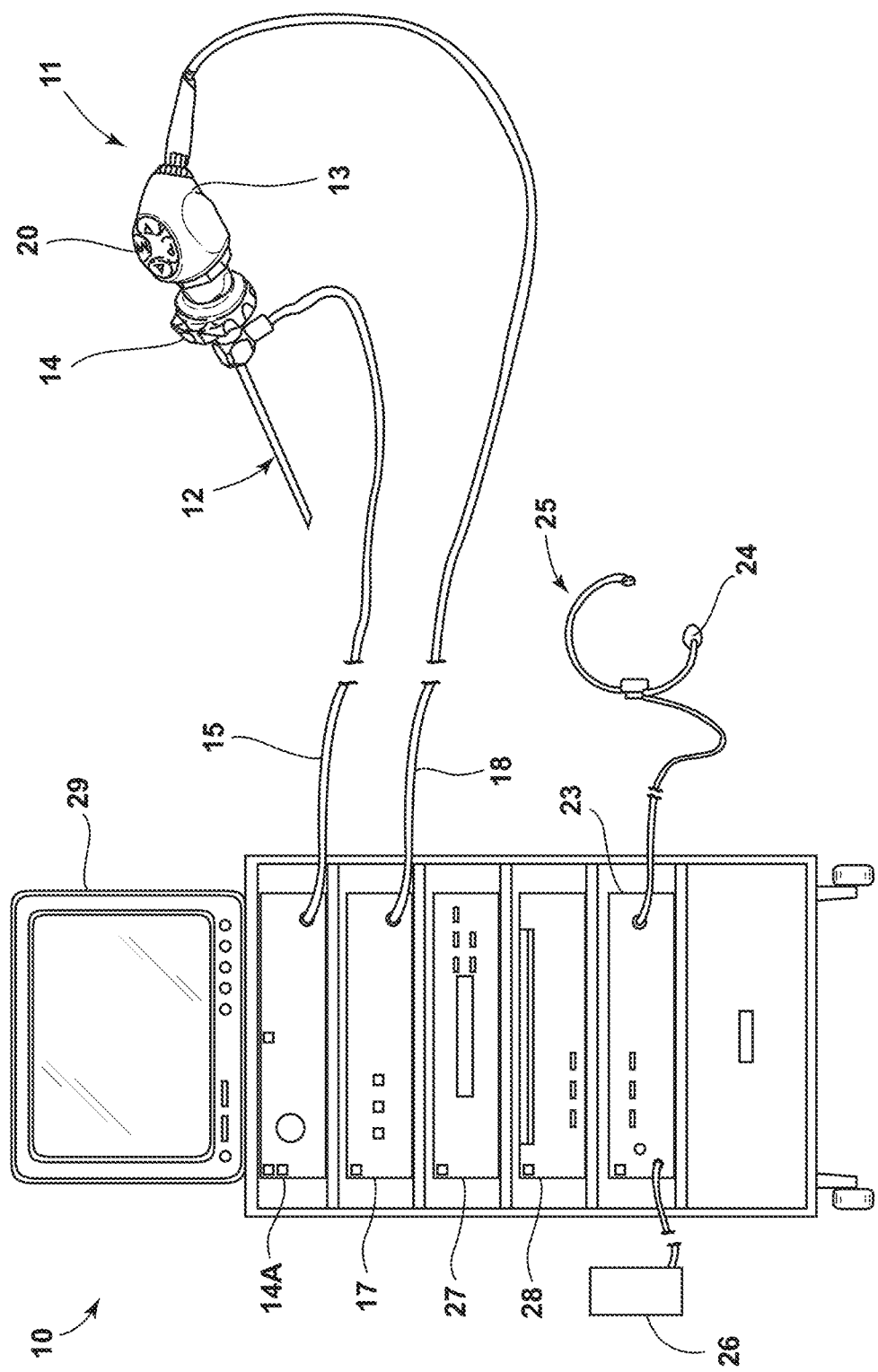
FIG. 1 is an illustration of an endoscopic imaging system comprising an endoscopic camera arrangement including an example of one type of camera assembly having a camera head with an integrated coupler arrangement incorporating a camera with automatic focusing according to an embodiment.
Figure 2:
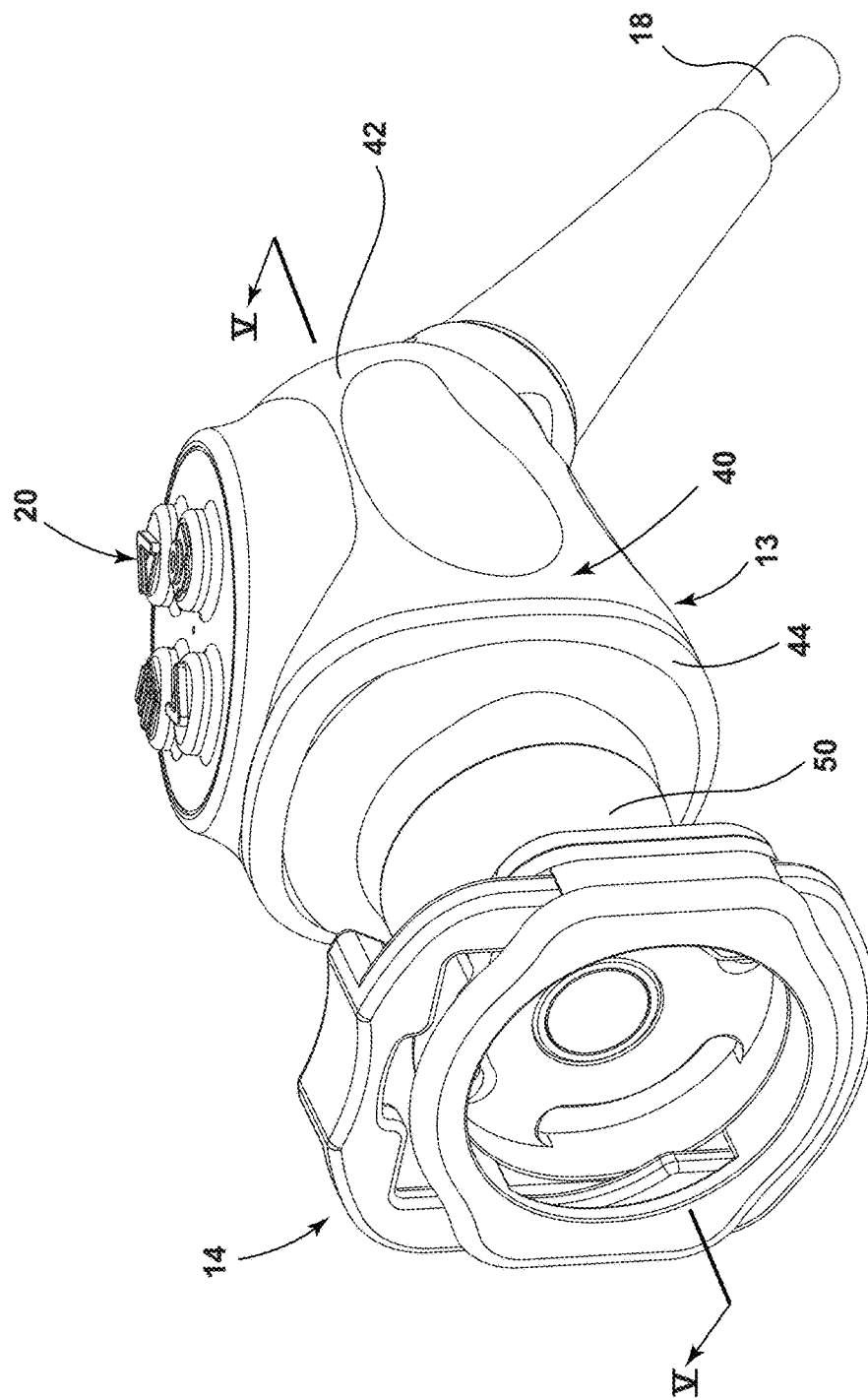
FIG. 2 is a perspective view of the camera head and coupler arrangement of FIG. 1.
Figure 3:
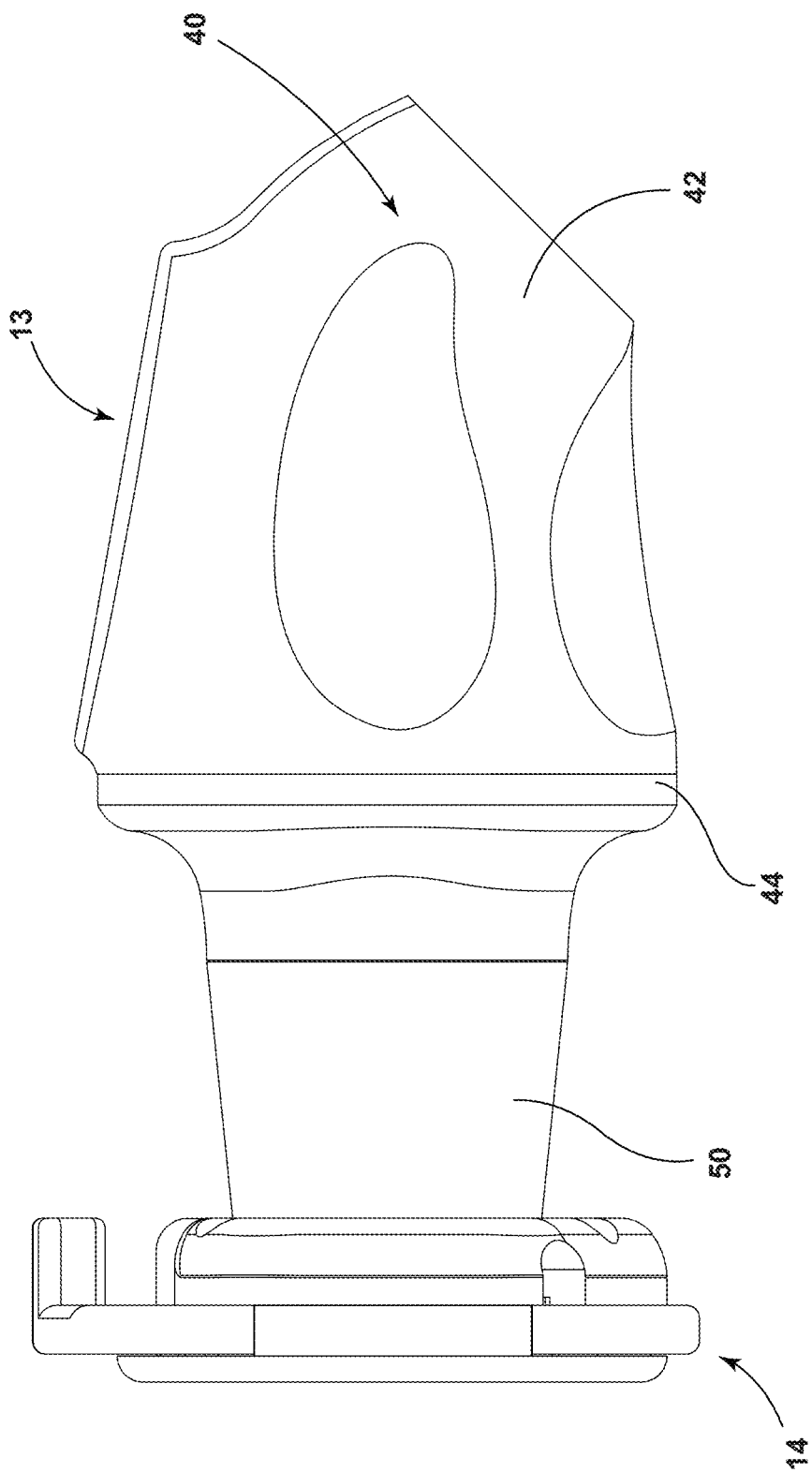
FIG. 3 is an elevated side view of the camera head and coupler arrangement of FIG. 2.

Reference will now be made in detail to implementations and various aspects and variations of the disclosure, examples of which are illustrated in the accompanying drawings. Although at least two variations of the systems, methods, and kits are described, other variations of the systems, methods, and kits may include aspects of the systems and methods described herein combined in any suitable manner having combinations of all or some of the aspects described.

Generally, corresponding or similar reference numbers will be used, when possible, throughout the drawings to refer to the same or corresponding parts. Certain terminology will be used in this description for convenience and reference only, and will not be limiting. For example, spatially relative terms such as "upwardly," "downwardly," "rightwardly," and "leftwardly" and the like will refer to directions in the drawings to which reference is made and may be used herein for ease of description to describe one element or feature's relationship to another element(s) or feature(s) as illustrated in the figures. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. This terminology will include the words specifically mentioned, derivatives thereof, and words of similar import. It will be understood that the spatially relative terms are intended to encompass different orientations of the system in use or operation in addition to the orientation depicted in the figures.

FIG. 1 shows an endoscopic camera arrangement 10, including a scope assembly 11, according to an embodiment, which may be utilized in endoscopic procedures. The scope assembly 11 incorporates an endoscope or scope 12 which is coupled to a camera head 13 by a coupler 14 located at the distal end of the camera head 13. Light is provided to the scope by a light source 14A via a light guide 15, such as a fiber optic cable. The camera head 13 is coupled to a camera control unit (CCU) 17 by an electrical cable 18. According to an embodiment, operation of the camera 13 is controlled, in part, by the CCU 17. The cable 18 conveys video image data from the camera head 13 to the CCU 17 and conveys various control signals bi-directionally between the camera head 13 and the CCU 17. In one embodiment, the image data output by the camera head 13 is digital, in which the cable 18 may be a FireWire, a universal serial bus (USB), or other type of high-speed digital interface.

In an embodiment, a control or switch arrangement 20 is provided on the camera head 13 and allows a user to manually control various functions of the arrangement 10. These and other functions may also be controlled by voice commands using a voice-control unit 23, which is coupled to the CCU 17. In an embodiment, voice commands are input into a microphone 24 mounted on a headset 25 worn by the surgeon and coupled to the voice-control unit 23. A hand-held control device 26, such as a tablet with a touch screen user interface or a PDA, may be coupled to the voice control unit 23 as a further control interface. In the illustrated embodiment, a recorder 27 and a printer 28 are also coupled to the CCU 17. Additional devices, such as an image capture and archiving device, may be included in the arrangement 10 and coupled to the CCU 17. Video image data acquired by the camera head 13 and processed by the CCU 17 is converted to images, which can be displayed on a monitor 29, recorded by recorder 27, and/or used to generate static images, hard copies of which can be produced by printer 28.

As shown in the embodiments in FIGS. 2-5, the camera head 13 includes a housing 40, which generally has three parts, a rear enclosure part 42, a front enclosure part 44, and a scope engagement device 14. The rear enclosure part 42 has a top cavity 46 for receiving the control or switch arrangement 20, which is attached to the rear enclosure part 42. The control or switch arrangement 20 includes magnets internal to the control or switch arrangement 20 that allow a button board 94 to sense button press user inputs through changes in magnetic field. The button board 94 resides internal to the rear enclosure 42.

The camera head unit 13, through the rear enclosure part 42, is attached to the electrical cable 18 for connection with the CCU 17, as described above.

The front enclosure part 44 includes a proximal portion 49 for attachment to the rear enclosure part 42 and a frusto-conical-shaped distal portion 50. The distal portion 50 is sized and shaped to house a lens system, which is described in more detail below.

The coupler or endoscope engagement device 14 can be any device suited for and capable of attachment to an endoscope or other surgical viewing device. It is preferably a spring-loaded structure that effectively clamps a scope to the camera head 13.

The distal end of the front enclosure part has an axially-extending annular lip 64 defining a space therein. A central hole 66 is within the confines of that space. The space defined by the annular lip 64 is sized and shaped to receive a window 68 which is preferably sealably attached to the front enclosure part 44.

Inside the camera housing 40 is a 3-chip camera sensor unit 88. The button board 94 receives signals from the button keypad 20. A cable 95 connects the button board 94 to the electrical cable 18.

Figure 4:
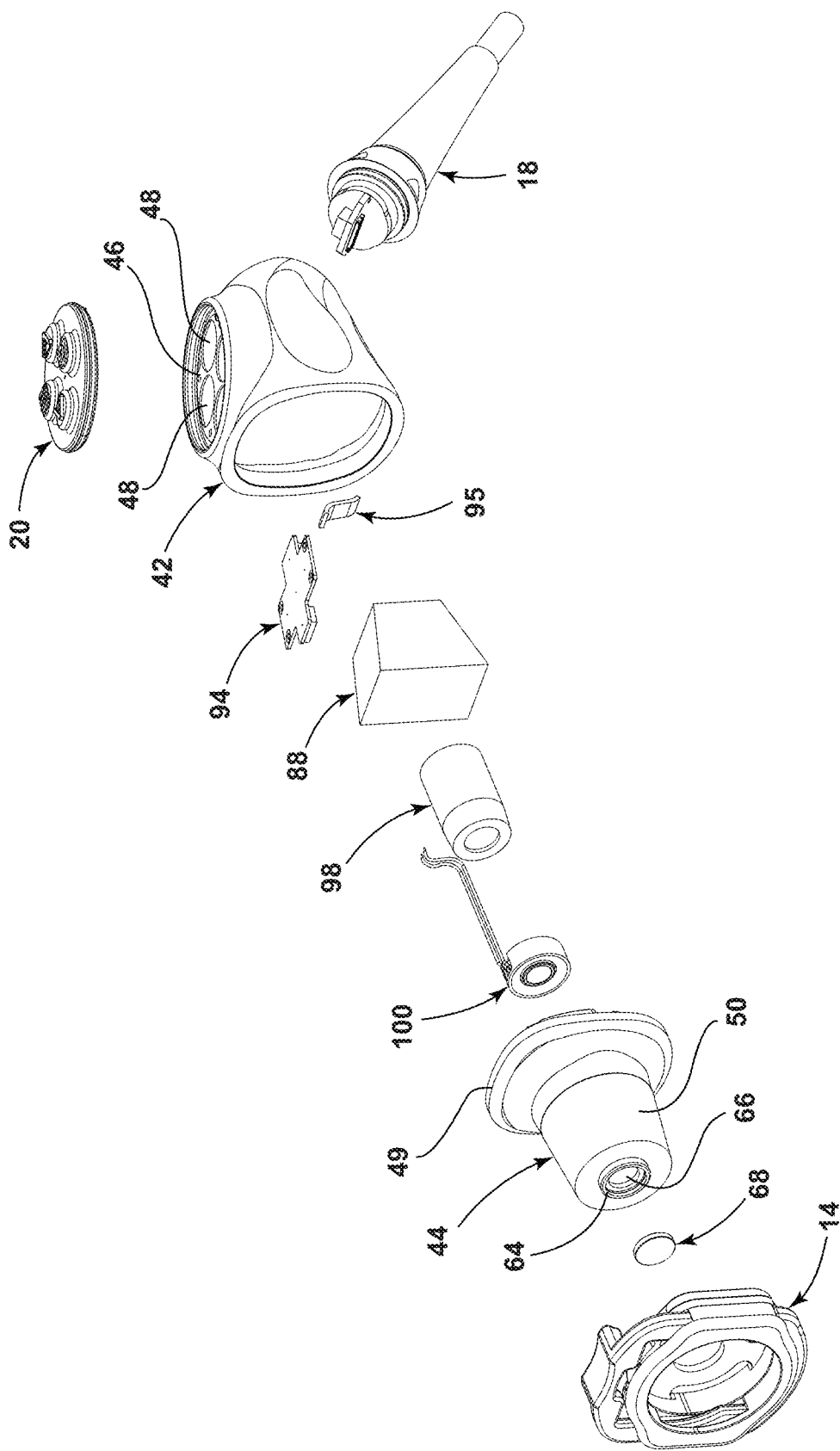
FIG. 4 is an exploded perspective view of the camera head and coupler arrangement of FIG. 2.
Figure 5:
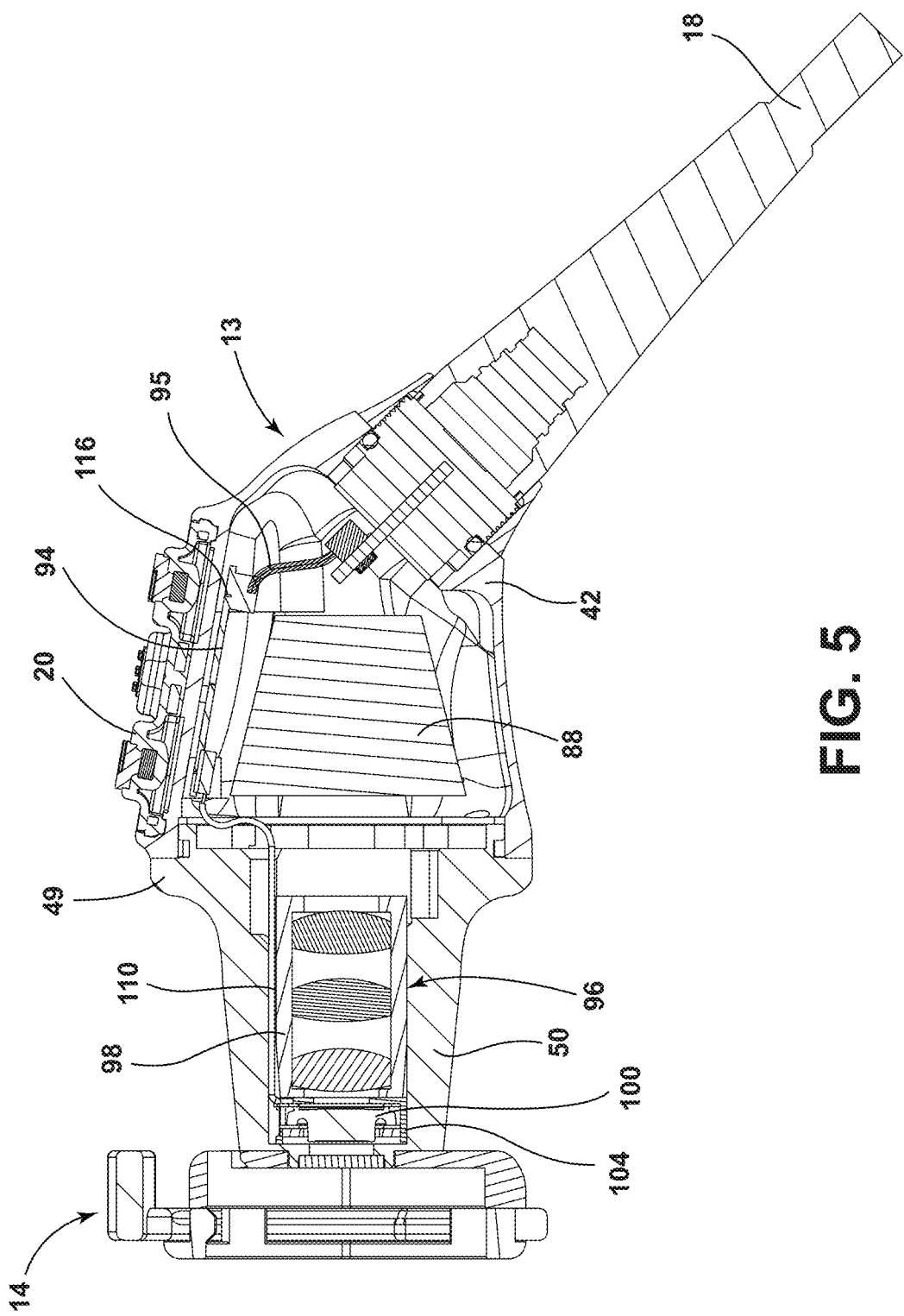
FIG. 5 is a side elevational cross-sectional view of the camera head and coupler arrangement of FIG. 2, taken along line V-V in FIG. 2.
Figure 6:
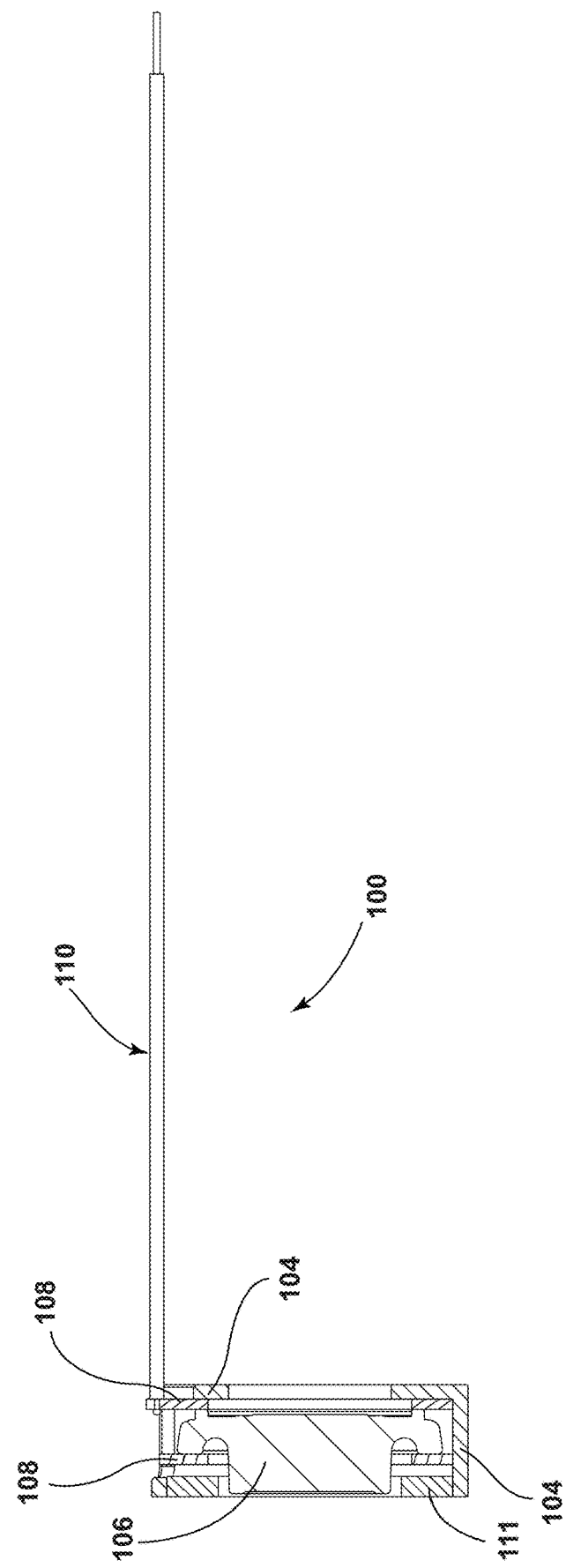
FIG. 6 is a side elevational cross-sectional view of the liquid lens assembly of the camera head and coupler arrangement of FIG. 2.

As shown in the embodiments in FIGS. 4 and 5, housed within the front enclosure part 44 is a lens system 96. Part of the lens system 96 may extend into the rear enclosure part 42. The lens system 96 includes a solid imaging lens 98, such as a glass lens assembly, and a liquid lens assembly 100, which is preferably positioned distally with respect to the solid lens assembly 98. The liquid lens assembly 100 is retained by a liquid lens housing 104. As shown in the embodiments in FIGS. 6-7, the liquid lens assembly 100 further includes a liquid lens module 106, one or more PCBs 108, a cable 110, and a housing cover 111.

In an embodiment, the liquid lens module 106 contains oil and water, which are immiscible, in a sealed cell. These liquids are preferable as water conducts electricity and oil is a polar. The liquid-liquid interface has a substantially spherical shape and the radius of curvature of the interface can be varied through application of voltage to the module. Voltage can be applied via the cable 110 by a liquid lens driver 116, located on the button board 94, to modify the surface tension of the conductive liquid on a solid surface, thereby changing the radius of curvature of the liquid-liquid interface. Changing the radius of curvature of the interface changes the optical power of the lens which refracts the light transmitted from a surgical scope and focuses the image.

In an embodiment, the liquid lens preferably has an optical power dynamic range of about twenty diopters. Because image quality with just a single liquid lens typically has spherical and chromatic aberrations, the addition of the solid lens assembly 98 is preferable. The solid lens assembly 98 aids in improving the quality of the image, providing a sharper image by effectively reducing spherical and chromatic aberrations, resulting in a focused image on the image sensor 88. It is contemplated that multiple solid lens assemblies could be used either in front or behind, or both, the liquid lens assembly 100 in the optical path.

In an embodiment, the CCU 17 contains an algorithm to analyze the image signal data received from the scope (after going through the lens assemblies 98, 100) to estimate the amount of misfocus and, based on that amount, to change the voltage applied across the liquid lens to achieve a focused image. The CCU 17 analyzes the data, estimates the amount of misfocus, sends a signal to the liquid lens driver (which optionally works in conjunction with a microcontroller to send a signal to the liquid lens assembly 100) with a determined adjusted voltage, then reanalyzes the image, estimates the amount of misfocus, determines if the misfocus improved or worsened, and repeats the voltage adjustments until the focused position is found. The algorithm can analyze the image to estimate the amount of misfocus by analyzing high frequency components within the image, analyzing contrast within the image, obtaining surgical scene information from the user preset, utilizing the last known lens position, and/or analyzing high frequency components in other predetermined areas of the image.

Figure 8:
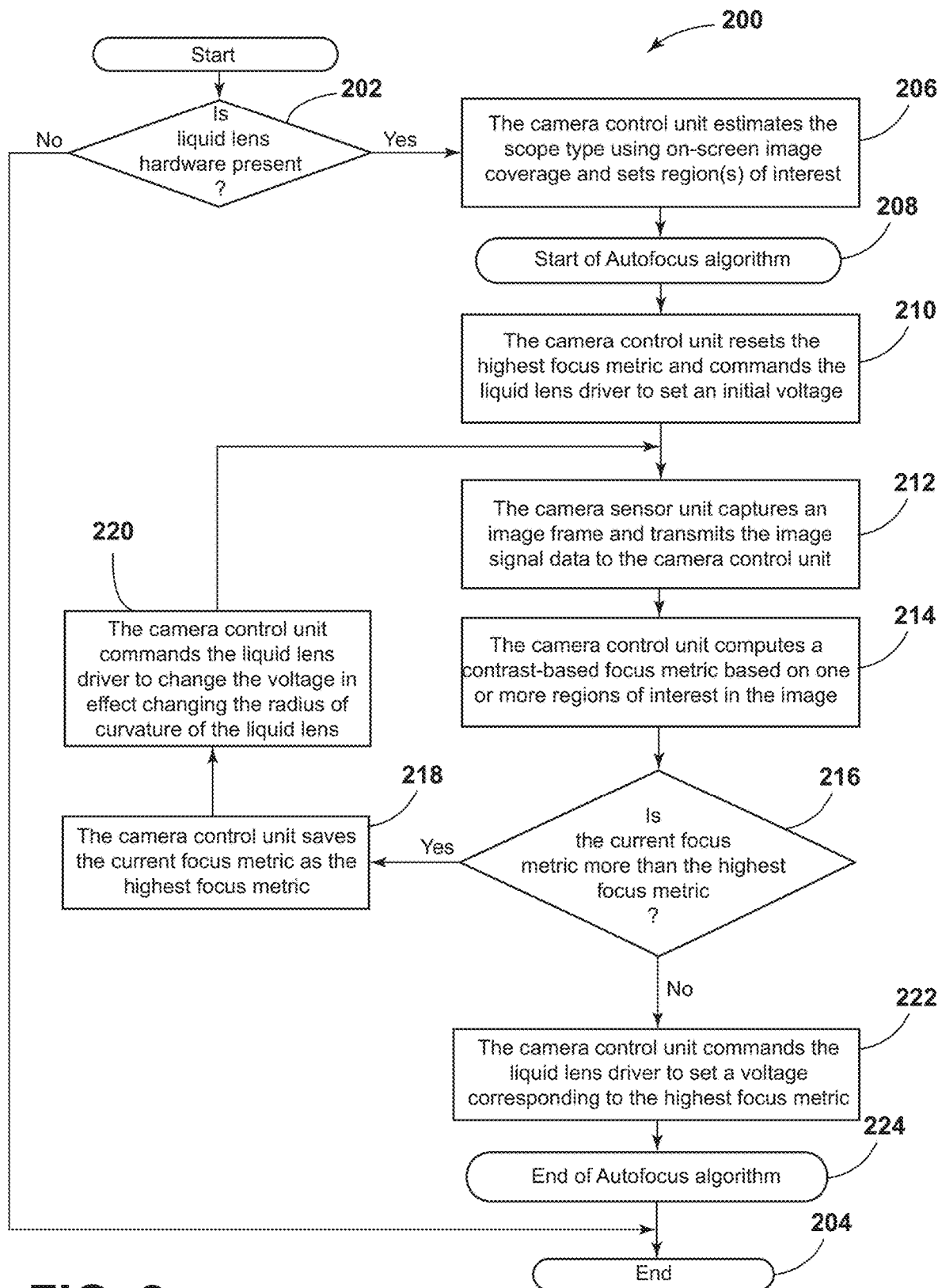
FIG. 8 is a flowchart of a voltage determination routine for the endoscopic camera arrangement of FIG. 1 according to an embodiment.

An exemplary flowchart 200 showing the general steps of such an algorithm is shown in FIG. 8. Specifically, the algorithm starts and then moves to a decision step 202 where it determines if liquid lens hardware is present in the system. If the answer is "NO," the algorithm goes to the end step 204 and stops. If the answer is "YES," the algorithm proceeds to step 206 at which the CCU 17 estimates the type of scope being used by determining the on-screen image coverage. The CCU 17 also sets the region(s) of interest in the image in this step 206.

The algorithm then proceeds to step 208, which is the start of the auto focus routine. Moving to step 210, the CCU 17 resets a highest focus metric and commands the liquid lens driver 116 to set an initial voltage. The focus metric is a measure and assigned value of how focused or "sharp" the image is.

Moving to step 212, the camera sensor unit 88 captures an image frame, converts the image frame to image signal data, and transmits the image signal data to the CCU 17. The CCU 17 then, in step 214, computes a contrast-based focus metric based on the one or more previously selected region(s) of interest in the image.

The algorithm then proceeds to decision step 216 where it is determined if the contrast-based focus metric of the image is more than the set highest focus metric.

If the current focus metric is higher than the set highest focus metric (i.e., the answer is "YES"), then the routine proceeds to step 218 wherein the CCU 17 saves (and thus resets) the highest focus metric as the value of the current focus metric. The routine then proceeds to step 220 where the CCU 17 commands the liquid lens driver 116 to change the voltage being delivered to the liquid lens module 106.

Figure 7:
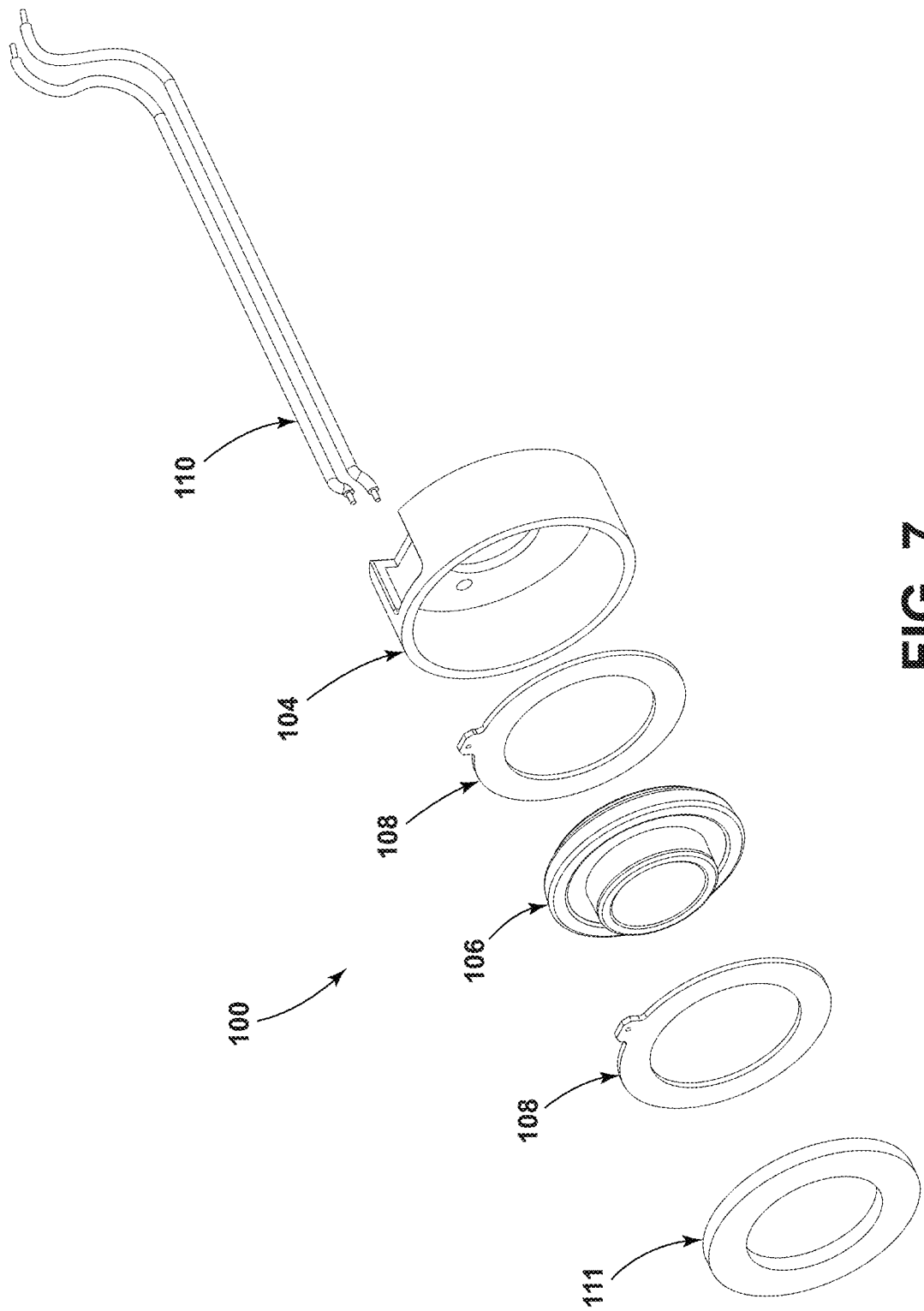
FIG. 7 is an exploded perspective view of the liquid lens assembly of FIG. 6.

The change in voltage (in what direction and in what quantity) is determined based on how many times the loop of the algorithm in FIG. 7 has been traversed for that particular focusing incident. At the start of the incident the voltage change will be in one direction (preferably a decrease, which causes the focus distance to increase) as the initial setting will be at one end of the diopter range. As the algorithm proceeds through the loop multiple times, the voltage is changed based on the focus metric history. Once the system determines that it has gone past a peak value for focus, it will change direction and magnitude (i.e. do a finer adjustment) to arrive back at the peak value of the focus metric. The change in voltage to the liquid lens module changes the radius of the curvature of the liquid lens liquid interface, thus changing the focus of the liquid lens 106.

The algorithm is then sent back to step 212 where another image frame is captured and converted to image signal data.

If the current focus metric is not higher than the set highest focus metric (i.e., the answer in decision step 216 is "NO"), then the algorithm proceeds to step 222 at which the CCU 17 commands the liquid lens driver 116 to set and deliver a voltage corresponding to the highest focus metric. The liquid lens driver 116 then delivers the commanded voltage to the liquid lens 106, and the auto focus algorithm is ended (at step 224).

The CCU 17 can achieve automatic image focusing through two modes: (1) a continuous search of the image focus, or (2) a trigger image focus. The continuous search has the CCU 17 continuously execute the focusing algorithm in real time to keep the image in focus at all times. If the scope is receiving an image of an object from a certain distance and the distance changes, the algorithm automatically adjusts the liquid lens to bring the new scene into focus. In the trigger image focus scenario, the CCU 17 uses the focusing algorithm only when triggered by user input to focus the image. This would typically be done by the user by pressing one or more buttons on the control or switch arrangement 20. If the distance of an image from the scope changes, bringing the image out of focus, the user provides an input (trigger) to activate the algorithm to adjust the liquid lens to bring the new scene into focus.

Because the system may be used with a variety of scopes which have varying diameters, the image sizes on a display monitor can vary. For example, a 10-mm laparoscope will cover about 76% optical diagonal of a sensor. However, a 4-mm arthroscope will only cover about 47% optical diagonal of the sensor.

Figure 9A:
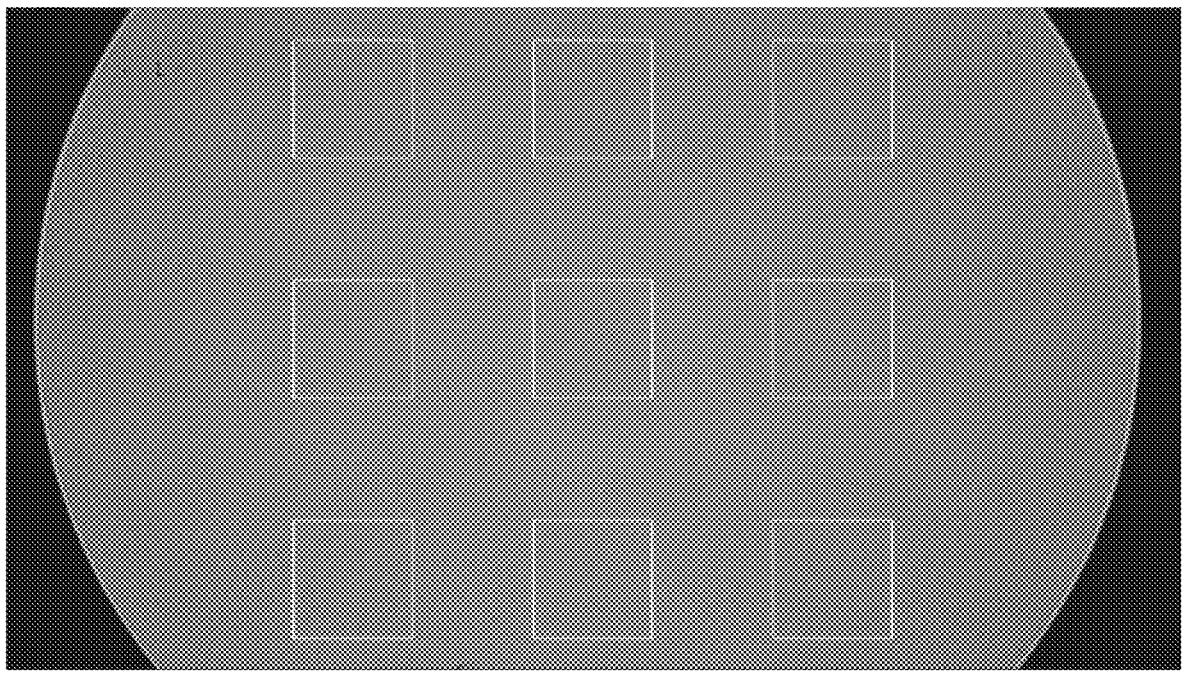
FIG. 9A is a photo of an electronic display screen with an image from a 10-mm laparoscope showing regions of interest.
Figure 9B:
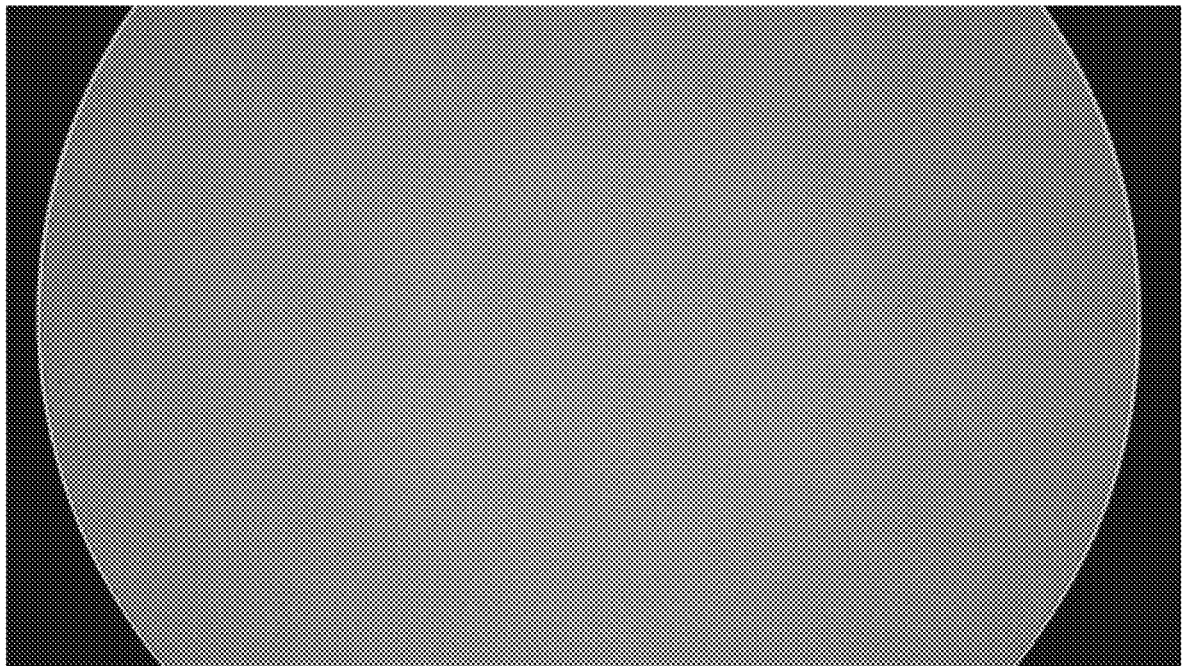
FIG. 9B is a photo of an electronic display screen with an image from a 10-mm laparoscope without regions of interest.
Figure 10A:
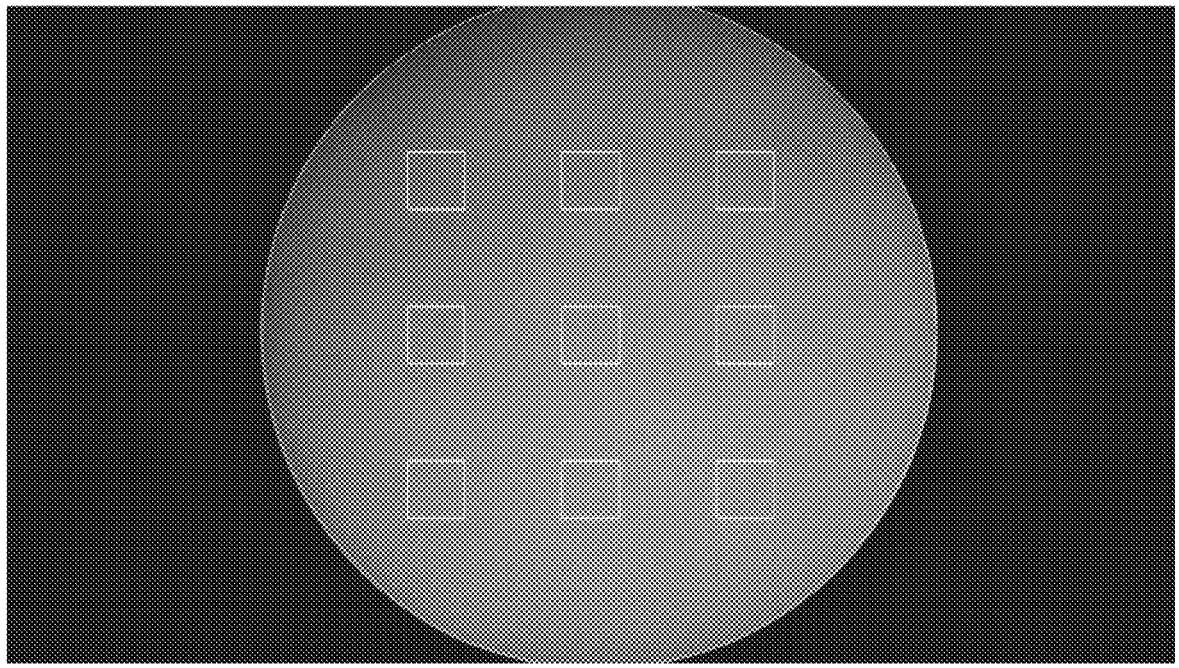
FIG. 10A is a photo of an electronic display screen with an image from a 4-mm arthroscope showing regions of interest.
Figure 10B:
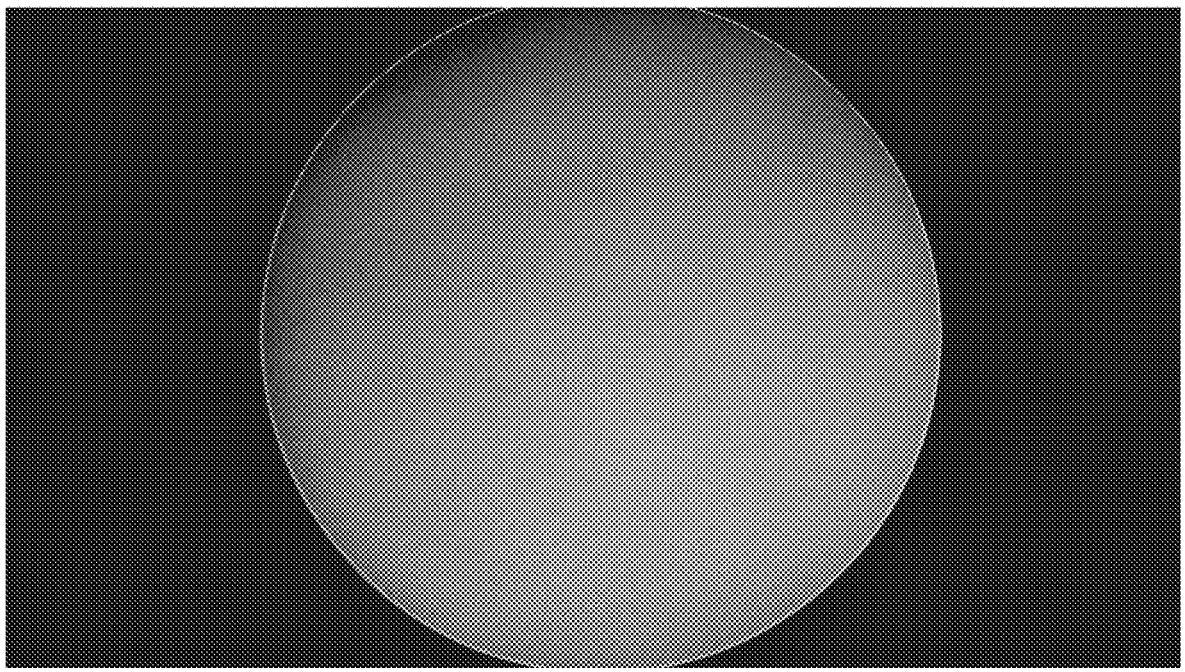
FIG. 10B is a photo of an electronic display screen with an image from a 4-mm arthroscope without regions of interest.

The present system detects sensor coverage. Once the sensor coverage is detected, the system will set the appropriate region of interest for contrast measurement. For example, nine square boxes are used as a region of interest for laparoscope contrast calculation (see FIG. 9A). FIG. 9B shows the size of the coverage for the laparoscope without the nine regions of interest boxes. For an arthroscope, because of the less sensor coverage, the size of the boxes and their location must be adjusted (see FIG. 10A). FIG. 10B shows the size of coverage for the arthroscope without the nine regions of interest boxes. At times, the image projected from the endoscope may not be perfectly aligned with the center of the sensor. The region of interest boxes can automatically adjust to align with the projected image sensor. This can further optimize the focus metric calculation.

The auto focus system described herein could be used in tandem with, or alternatively to, a manual focusing system featured on the same camera. Such a manual focusing system could be any type of focusing device requiring manual user input, including, but not limited to, a knob, a slider, or a button on the control 20.

The liquid lens focus system provides a surgeon or other medical professional a focused image that is achieved rapidly without mechanical input and adjustment. Such a system can have a continuous, automatic focusing feature or a trigger, user-driven focusing feature. Thus, without the use of mechanics, the system can provide a flexible and accurate focusing system to be used during an endoscopic procedure.

In use, a camera head assembly with a liquid lens, such as the one described above, an image sensor, and a liquid lens driver is provided in a medical or surgical setting. A camera control unit is also provided, the camera control unit (CCU) including an algorithm, such as the one described above, capable of calculating a desired voltage for the liquid lens and transmitting a signal to the liquid lens driver.

An image passes through the liquid lens and to the image sensor. The image sensor converts the image to data based on characteristics of the image, and transmits the data to the CCU.

The algorithm in the CCU analyzes the data and, based on this analysis, forwards a signal to the liquid lens driver. The liquid lens driver then transmits a voltage to the liquid lens based on the signal received from the CCU to better focus the image.

Example Imaging Agents for Use with the Methods and Systems for Endoscopic Surgery Visualization In various embodiments, the systems and methods described herein may be used in medical imaging comprising various optical modalities such as for example, white light imaging, fluorescence imaging, or a combination thereof. In an embodiment comprising fluorescence medical imaging applications, an imaging agent for use in combination with the method and systems described herein is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

In some embodiments, the fluorescence imaging agent may be administered in various concentrations to achieve a desired circulating concentration in the blood or in other body tissue or fluid into which the fluorescence agent is administered. For example, in embodiments where the fluorescence imaging agent is ICG, it may be administered at a concentration of about 2.5 mg/mL to achieve a circulating concentration of about 5 $\mu$M to about 10 $\mu$M in blood. In various embodiments, the upper concentration limit for the administration of the fluorescence imaging agent is the concentration at which the fluorescence imaging agent becomes clinically toxic in circulating blood or other body tissue or fluid, and the lower concentration limit is the instrumental limit for acquiring the signal intensity data arising from the fluorescence imaging agent circulating with blood or in other body tissue or fluid to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 $\mu$M to about 10 mM. Thus, in one aspect, the methods described herein may comprise the step of administration of the imaging agent (e.g., a fluorescence imaging agent) to the subject and acquisition of the signal intensity data (e.g., video) prior to processing the signal intensity data. In another aspect, the method may exclude any step of administering the imaging agent to the subject.

In an embodiment, a suitable fluorescence imaging agent for use in fluorescence imaging applications alone or in combination with other imaging to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In some variations, the fluorescence imaging agent comprises a fluorescence dye, an analogue thereof, a derivative thereof, or a combination of these. A fluorescence dye includes any non-toxic fluorescence dye. In certain embodiments, the fluorescence dye emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In an embodiment, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe for use as a kit with the systems and methods described herein. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some variations, the fluorescence imaging agent used in combination with the methods, systems and kits described herein may be used for blood flow imaging, tissue perfusion imaging, lymphatic imaging, or a combination thereof, or to image tissue or a body structure (e.g., urinary system imaging including ureter imaging) which may performed during an invasive surgical procedure, a minimally invasive surgical procedure, or a non-invasive surgical procedure in combination with invasive and minimally invasive procedures. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In some variations relating to any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts, or other vessels. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30 G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG dose may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc- 99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

In various embodiments, the methods and systems may be used for tissue perfusion imaging. Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A surgical camera system comprising:
an endoscopic camera head including a housing comprising a rear enclosure portion and a front enclosure portion connected to the rear enclosure portion, the front enclosure portion comprising an endoscopic coupler for coupling an endoscope to the endoscopic camera head;
an image sensor within the rear enclosure portion of the housing; and
the front enclosure portion of the housing including a liquid lens therein for focusing an image received in the front enclosure portion of the housing prior to transmission of the image to the image sensor, and a fixed solid lens adjacent the liquid lens within the front enclosure portion,
wherein the surgical camera system is configured to:
detect a coverage of the image sensor by light projected by the endoscope into the endoscopic camera head,
set a region of interest based on the detected coverage,
calculate a focus metric within the region of interest, and
based on the focus metric, control the liquid lens to adjust the focus of the endoscopic camera head.

2. The surgical camera system of claim 1, wherein the liquid lens is positioned distally with respect to the solid lens.

3. The surgical camera system of claim 1, further comprising a liquid lens cable in electrical communication with the liquid lens and capable of communicating an electrical signal for use in adjusting focus of the liquid lens.

4. The surgical camera system of claim 3, further comprising a camera control unit which receives and analyzes image data to determine a voltage for the electrical signal to be delivered to the liquid lens via a driver.

5. A kit for imaging tissue of a subject, the kit comprising a fluorescence imaging agent and the surgical camera system of claim 1.

6. A surgical camera system comprising:
a camera assembly including a housing having an outer wall defining a space in the housing, wherein the housing comprises a rear enclosure portion and a front enclosure portion connected to the rear enclosure portion, the front enclosure portion comprising an endoscopic coupler for coupling an endoscope to an endoscopic camera head of the camera assembly;
an image sensor disposed within the rear enclosure portion of the housing;
an optical path within the housing capable of allowing an optical image to travel from a surgical site to the image sensor; and
at least one lens assembly within the optical path and within the front enclosure portion of the housing, the at least one lens assembly including a liquid lens and at least one fixed solid lens adjacent the liquid lens within the front enclosure portion,
wherein the surgical camera system is configured to:
detect a coverage of the image sensor by light projected by the endoscope into the endoscopic camera head,
set a region of interest based on the detected coverage,
calculate a focus metric within the region of interest, and
based on the focus metric, control the liquid lens to adjust the focus of the endoscopic camera head.

7. The surgical camera system of claim 6, wherein the solid lens is a glass lens.

8. The surgical camera system of claim 6, wherein the liquid lens is positioned distally with respect to the solid lens.

9. The surgical camera system of claim 6, further comprising a liquid lens cable in communication with the liquid lens and capable of communicating an electrical signal for adjusting the focus of the liquid lens.

10. The surgical camera system of claim 6, wherein the surgical camera system configured to automatically adjust the size, location and centering of the region of interest.

11. The surgical camera system of claim 6, further comprising a driver in the housing for converting a signal into a voltage and delivering the voltage to the liquid lens.

12. A method comprising performing lymphatic imaging, blood flow imaging, tissue perfusion imaging, or a combination thereof using a surgical camera system that comprises:
an endoscopic camera head including a housing comprising a rear enclosure portion and a front enclosure portion connected to the rear enclosure portion, the front enclosure portion comprising an endoscopic coupler for coupling an endoscope to the endoscopic camera head,
an image sensor within the rear enclosure portion of the housing,
wherein the front enclosure portion of the housing includes a liquid lens therein for focusing an image received in the front enclosure portion of the housing prior to transmission of the image to the image sensor, and a fixed solid lens adjacent the liquid lens within the front enclosure portion,
wherein the surgical camera system is configured to:
detect a coverage of the image sensor by light projected by the endoscope into the endoscopic camera head,
set a region of interest based on the detected coverage,
calculate a focus metric within the region of interest, and
based on the focus metric, control the liquid lens to adjust the focus of the endoscopic camera head.

13. A method comprising performing lymphatic imaging, blood flow imaging, tissue perfusion imaging, or a combination thereof using a fluorescence imaging agent provided in a kit and a surgical camera system provided in the kit, the surgical camera system comprising:
an endoscopic camera head including a housing comprising a rear enclosure portion and a front enclosure portion connected to the rear enclosure portion, the front enclosure portion comprising an endoscopic coupler for coupling an endoscope to the endoscopic camera head,
an image sensor within the rear enclosure portion of the housing,
wherein the front enclosure portion of the housing includes a liquid lens therein for focusing an image received in the front enclosure portion of the housing prior to transmission of the image to the image sensor, and a fixed solid lens adjacent the liquid lens within the front enclosure portion,
wherein the surgical camera system is configured to:
detect a coverage of the image sensor by light projected by the endoscope into the endoscopic camera head,
set a region of interest based on the detected coverage, calculate a focus metric within the region of interest, and based on the focus metric, control the liquid lens to adjust the focus of the endoscopic camera head.

\* \* \* \* \*